US011666748B2

(12) United States Patent
Kronstedt et al.

(10) Patent No.: US 11,666,748 B2
(45) Date of Patent: Jun. 6, 2023

(54) HYBRID BEARING SEAL FOR USE IN BLOOD PUMP

(71) Applicant: Boston Scientific Scimed Inc, Maple Grove, MN (US)

(72) Inventors: Joseph A. Kronstedt, New Hope, MN (US); Umang Anand, Plymouth, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 60 days.

(21) Appl. No.: 17/004,112

(22) Filed: Aug. 27, 2020

(65) Prior Publication Data

US 2021/0060224 A1 Mar. 4, 2021

Related U.S. Application Data

(60) Provisional application No. 62/894,059, filed on Aug. 30, 2019.

(51) Int. Cl.
*A61M 60/422* (2021.01)

(52) U.S. Cl.
CPC ... *A61M 60/422* (2021.01); *A61M 2205/0266* (2013.01); *A61M 2205/3646* (2013.01); *A61M 2205/50* (2013.01)

(58) Field of Classification Search
CPC .............. A61M 60/827; A61M 60/205; A61M 60/422; A61M 2205/0266; A61M 2205/3646; A61M 2205/50; A61M 60/221; A61M 60/13; F04D 29/04; F04D 29/58; F04D 29/5806; F04D 29/586; F04D 29/588; F04D 29/5893
See application file for complete search history.

(56) References Cited

U.S. PATENT DOCUMENTS

| | | | | | |
|---|---|---|---|---|---|
| 4,704,121 | A | * | 11/1987 | Moise | A61M 60/205 623/3.13 |
| 5,531,789 | A | * | 7/1996 | Yamazaki | A61M 60/829 623/23.68 |
| 6,302,910 | B1 | * | 10/2001 | Yamazaki | A61M 60/17 623/3.1 |
| 8,900,060 | B2 | * | 12/2014 | Liebing | A61M 60/122 464/7 |
| 10,030,670 | B2 | * | 7/2018 | Bratthall | H02K 5/225 |

FOREIGN PATENT DOCUMENTS

JP H07178163 A * 7/1995 .......... A61M 60/237

* cited by examiner

*Primary Examiner* — Eldon T Brockman
*Assistant Examiner* — Maxime M Adjagbe
(74) *Attorney, Agent, or Firm* — Faegre Drinker Biddle & Reath LLP

(57) ABSTRACT

A seal assembly is configured to seal a portion of a blood pump from the blood. The seal assembly includes a first seal; and a second seal. The second seal includes a lower contact-pressure seal than the first seal.

18 Claims, 2 Drawing Sheets

HYBRID BEARING SEAL FOR USE IN BLOOD PUMP

CROSS REFERENCE TO RELATED APPLICATION

This application claims priority to Provisional Application No. 62/894,059, filed Aug. 30, 2019, which is herein incorporated by reference in its entirety.

TECHNICAL FIELD

The present disclosure relates to circulatory support devices. More specifically, the disclosure relates to seal assemblies used in circulatory support devices.

BACKGROUND

Circulatory support devices such as blood pumps typically provide circulatory support for up to approximately three weeks of continuous use. Friction at seal-housing interfaces can generate heat, which can lead to hemolysis, which can further lead to health complications such as anemia, requiring blood transfusions.

SUMMARY

In an Example 1, a seal assembly configured to seal a portion of a blood pump from the blood, the seal assembly comprising: a first seal; and a second seal, the second seal comprising a lower contact-pressure seal than the first seal.

In an Example 2, the seal assembly of Example 1, further comprising a volume of lubricant disposed between the first seal and the second seal.

In an Example 3, the seal of assembly of Example 2, wherein the seal assembly is configured so that heat created by the second seal is dissipated into the lubricant and/or a housing of the blood pump.

In an Example 4, the seal of assembly of any of Examples 1-3, wherein the first seal comprises a bearing configured to receive an end of at least a portion of a drive shaft of the blood pump.

In an Example 5, the seal assembly of Example 4, wherein the end of the at least a portion of the drive shaft is at least partially rounded, and the bearing comprises a concave depression defined in a first side of the bearing, wherein the depression is configured to receive the end of the drive shaft.

In an Example 6, the seal assembly of Example 5, the bearing further comprising a shaft aperture defined therein, extending from the second side of the bearing to the first side of the bearing, wherein the shaft aperture is configured to receive a portion of the drive shaft.

In an Example 7, a blood pump, comprising: an impeller assembly having an impeller disposed within an impeller assembly housing; a drive shaft coupled to the impeller and configured to rotate with the impeller; a motor, disposed within a motor housing and configured to drive the impeller; and a seal assembly comprising a plurality of seals, the plurality of seals comprising a first seal and a second seal, the second seal comprising a lower contact-pressure seal than the first seal.

In an Example 8, the blood pump of Example 7, further comprising a volume of lubricant disposed between the first seal and the second seal.

In an Example 9, the blood pump of Example 8, wherein the seal assembly is configured so that heat created by the second seal is dissipated into the lubricant and/or impeller assembly housing.

In an Example 10, the blood pump of any of Examples 7-9, wherein the first seal comprises a bearing configured to receive an end of at least a portion of the drive shaft.

In an Example 11, the blood pump of Example 10, wherein the end of the at least a portion of the drive shaft is at least partially rounded, and the bearing comprises a concave depression defined in a first side of the bearing, wherein the depression is configured to receive the end of the drive shaft.

In an Example 12, the blood pump of Example 11, the bearing further comprising a shaft aperture defined therein, extending from the second side of the bearing to the first side of the bearing, wherein the shaft aperture is configured to receive a portion of the drive shaft.

In an Example 13, the blood pump of any of Examples 10-12, further comprising a biasing feature configured to bias the bearing toward the impeller, the biasing feature comprising a spring disposed between the second side of the bearing and a spring retainer, wherein the spring surrounds a portion of the drive shaft.

In an Example 14, the blood pump of any of Examples 1-13, wherein the motor housing is coupled to the impeller assembly housing, wherein the seal assembly is configured to seal the motor from the blood.

In an Example 15, the blood pump of any of Examples 1-13, wherein the motor housing is separate from the impeller assembly housing, the drive shaft comprising a first portion and a second portion, wherein the first portion is a drive line disposed within a protective tube, the drive line extending between the motor housing and the impeller assembly housing, wherein the seal assembly is configured to seal the drive line from the blood.

In an Example 16, a seal assembly configured to seal a portion of a blood pump from the blood, the seal assembly comprising: a first seal; and a second seal, the second seal comprising a lower contact-pressure seal than the first seal.

In an Example 17, the seal assembly of Example 16, further comprising a volume of lubricant disposed between the first seal and the second seal.

In an Example 18, the seal of assembly of Example 17, wherein the seal assembly is configured so that heat created by the second seal is dissipated into the lubricant and/or a housing of the blood pump.

In an Example 19, the seal of assembly of Example 16, wherein the first seal comprises a bearing configured to receive an end of at least a portion of a drive shaft of the blood pump.

In an Example 20, the seal assembly of Example 19, wherein the end of the at least a portion of the drive shaft is at least partially rounded, and the bearing comprises a concave depression defined in a first side of the bearing, wherein the depression is configured to receive the end of the drive shaft.

In an Example 21, the seal assembly of Example 20, the bearing further comprising a shaft aperture defined therein, extending from the second side of the bearing to the first side of the bearing, wherein the shaft aperture is configured to receive a portion of the drive shaft.

In an Example 22, the seal assembly of Example 19, further comprising a biasing feature configured to bias the bearing toward the impeller.

In an Example 23, the seal assembly of Example 22, the biasing feature comprising a spring disposed between the second side of the bearing and a spring retainer, wherein the spring surrounds a portion of the drive shaft.

In an Example 24, the seal assembly of Example 16, wherein the seal assembly is disposed in an impeller assembly housing, wherein a drive shaft, having a first portion and a second portion, extends between the impeller assembly housing and a motor housing, wherein the first portion is a drive line disposed within a protective tube, the drive line extending between the motor housing and the impeller assembly housing, wherein the seal assembly is configured to seal the drive line from the blood.

In an Example 25, a blood pump, comprising: an impeller assembly having an impeller disposed within an impeller assembly housing; a drive shaft coupled to the impeller and configured to rotate with the impeller; a motor, disposed within a motor housing and configured to drive the impeller; and a seal assembly comprising a plurality of seals, the plurality of seals comprising a first seal and a second seal, the second seal comprising a lower contact-pressure seal than the first seal.

In an Example 26, the blood pump of Example 25, further comprising a volume of lubricant disposed between the first seal and the second seal.

In an Example 27, the blood pump of Example 26, wherein the seal assembly is configured so that heat created by the second seal is dissipated into the lubricant and/or impeller assembly housing.

In an Example 28, the blood pump of Example 25, wherein the first seal comprises a bearing configured to receive an end of at least a portion of the drive shaft.

In an Example 29, the blood pump of Example 28, wherein the end of the at least a portion of the drive shaft is at least partially rounded, and the bearing comprising a concave depression defined in a first side of the bearing, wherein the depression is configured to receive the end of the drive shaft.

In an Example 30, the blood pump of Example 29, the bearing further comprising a shaft aperture defined therein, extending from the second side of the bearing to the first side of the bearing, wherein the shaft aperture is configured to receive a portion of the drive shaft.

In an Example 31, the blood pump of Example 28, further comprising a biasing feature configured to bias the bearing toward the impeller.

In an Example 32, the blood pump of Example 31, the biasing feature comprising a spring disposed between the second side of the bearing and a spring retainer, wherein the spring surrounds a portion of the drive shaft.

In an Example 33, the blood pump of Example 25, wherein the motor housing is coupled to the impeller assembly housing, wherein the seal assembly is configured to seal the motor from the blood.

In an Example 34, the blood pump of Example 25, wherein the motor housing is separate from the impeller assembly housing, the drive shaft comprising a first portion and a second portion, wherein the first portion is a drive line disposed within a protective tube, the drive line extending between the motor housing and the impeller assembly housing, wherein the seal assembly is configured to seal the drive line from the blood.

In an Example 35, a blood pump, comprising: an impeller assembly having an impeller disposed within an impeller assembly housing; a drive shaft coupled to the impeller and configured to rotate with the impeller; a motor, disposed within a motor housing and configured to drive the drive shaft; and a seal assembly disposed within the impeller assembly housing and comprising a plurality of seals, the plurality of seals comprising a first seal and a second seal, the second seal comprising a lower contact-pressure seal than the first seal.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
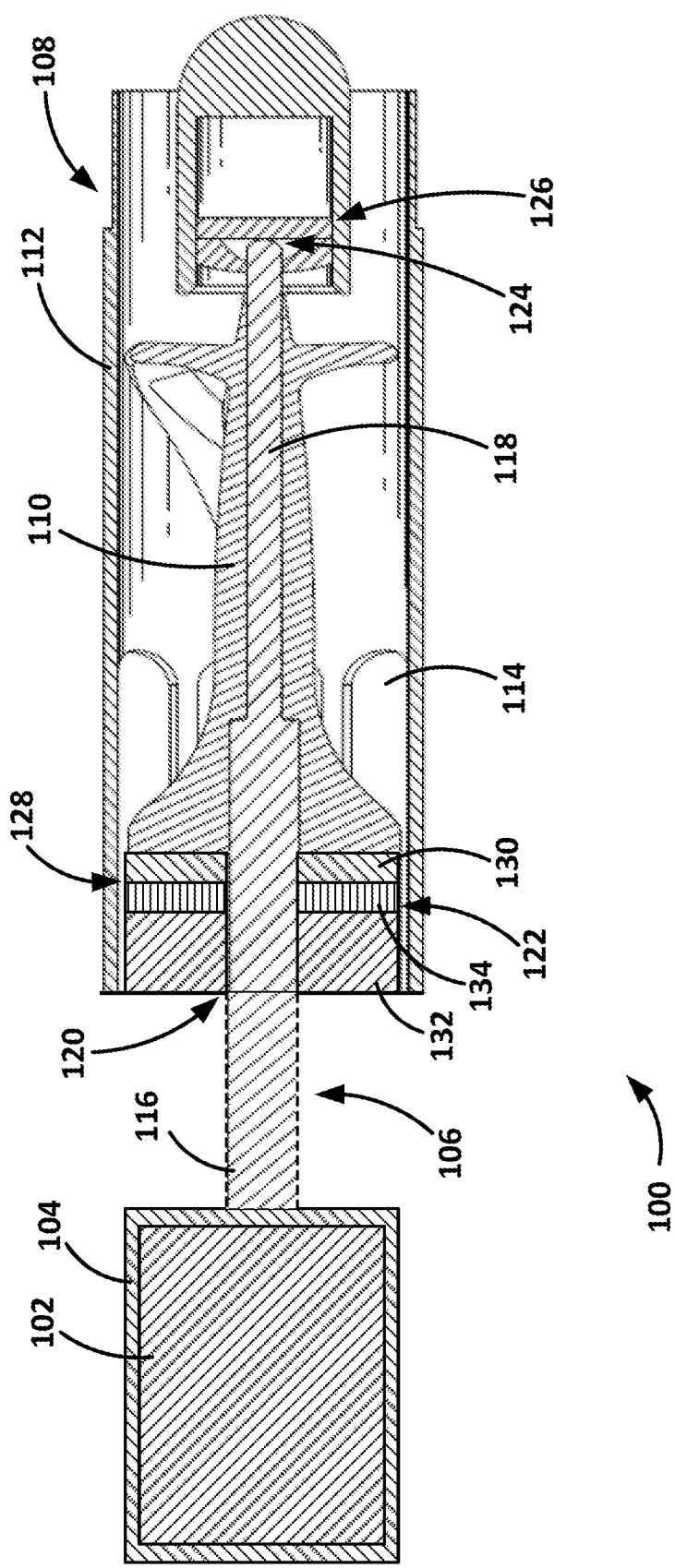
FIG. 1 depicts a cross-sectional side view of a portion of an illustrative mechanical circulatory support device (also referred to herein, interchangeably, as a "blood pump"), in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

DETAILED DESCRIPTION

Embodiments include a mechanical circulatory support device having at least two rotary seals, one of which is a high contact-pressure seal and another of which is a low contact-pressure seal. In embodiments, the high contact-pressure seal is disposed proximal to the low contact-pressure seal and a lubricant is disposed between the high contact-pressure seal and the low contact-pressure seal. Embodiments of the arrangement of high and low contact-pressure seals may facilitate keeping temperatures lower, thereby reducing hemolysis and thrombosis. In embodiments, the blood pump may include a ball and cup type bearing which acts as a seal between the blood environment and the motor.

FIG. 1 depicts a cross-sectional side view of a portion of an illustrative mechanical circulatory support device 100 (also referred to herein, interchangeably, as a "blood pump"), in accordance with embodiments of the subject matter disclosed herein. As shown in FIG. 1, the circulatory support device 100 includes a motor 102 disposed within a motor housing 104. The motor 102 is configured to drive, via a drive shaft 106, an impeller assembly 108 to provide a flow of blood through the impeller assembly 108. The impeller assembly 108 includes an impeller 110 disposed within an impeller assembly housing 112, which includes a number of outlet apertures 114 defined therein. The impeller assembly 108, as shown, also includes the drive shaft 106 (or at least a portion thereof), where the drive shaft 106 is configured to rotate with the impeller 110. As shown, the drive shaft 106 is at least partially disposed within the impeller 110. In embodiments, the drive shaft 106 may be made of any number of different rigid materials such as, for example, steel, titanium alloys, cobalt chromium alloys, nitinol, high-strength ceramics, and/or the like. In embodiments, the motor 102 may be configured to drive the impeller 110 via a magnetic coupling, rather than via driving the drive shaft 106.

According to embodiments, the motor housing 104 and the impeller assembly housing 112 may be integrated with one another. In other embodiments, the motor housing 104 and the impeller assembly housing 112 may be separate components configured to be coupled together, either removeably or permanently. In still other embodiments, the motor housing 104 may be configured to be separate from the impeller assembly housing 112. For example, in embodiments, the motor housing 104 may be configured to be disposed outside of a subject's body, while the impeller assembly 108 is disposed within the subject's body. In these embodiments, at least a portion of the drive shaft 106 may be configured as a flexible or semi-flexible wire, known as a drive line, which may be disposed within a protective tube that extends from the motor housing 104 to the impeller assembly housing 112. That is, for example, a first portion 116 of the drive shaft 106 may be a wire configured to extend from the motor 102 to the impeller assembly 108, where it is coupled to a second portion 118 of the drive shaft 106, which may, in embodiments, be configured as a solid shaft extending through at least a portion of the impeller 110.

As shown, the impeller 110 is maintained in its orientation by the drive shaft 108 (or, in the case of wire-driven impeller assemblies 108, the second portion 118 of the drive shaft 106), which is retained, at a first end 120, by a first bearing assembly 122 and, at a second end 124, by a second bearing assembly 126. According to embodiments, the first bearing assembly 122 and the second bearing assembly 126 may include different types of bearings. According to embodiments, the first bearing assembly 122 and/or the second bearing assembly 126 may include lubrication, while, in other embodiments, one and/or the other may not include lubrication.

According to embodiments, the device 100 may include a seal assembly 128 having a plurality of seals configured to seal the motor 102 and/or one or more bearings from the blood. In embodiments, the seals may be independent of the first bearing assembly 122. According to embodiments, the plurality of seals may include seals of different contact pressures, which may include, for example, high contact-pressure seals and low contact-pressure seals. For example, in embodiments, the impeller assembly 108 may include a first seal 130 and a second seal 132. A volume of lubricant 134 may be disposed between the first seal 130 and the second seal 132. In embodiments, the first seal 130 may be a low contact-pressure seal and the second seal 132 may be a high contact-pressure seal.

In embodiments, "high" and "low" may be defined in terms of each other. That is, for example, a high contact-pressure seal is one that has a higher contact pressure with the impeller assembly housing 112 and/or motor housing 104 than a low contact-pressure seal, which has a lower contact-pressure than the high contact-pressure seal. In embodiments, the high contact-pressure seal may be configured such that it completely seals (or at least approximately completely seals), from the blood, the motor 102, one or more bearings, a coupling between a first and second portions of a drive shaft, the first portion of the drive shaft (e.g., a drive line), and/or the like. As used herein in association with respect to characteristics (e.g., dimensions, measurements, attributes, components, etc.) of a seal, "about" and "approximately" may be used, interchangeably, to refer to a characteristic that is equal to (or the same as) the stated characteristic or equal to (or the same as) a characteristic that is reasonably close to the stated characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

In embodiments, the low contact-pressure seal 130 may be configured to thermally isolate the high contact-pressure seal 132 from the blood, alone, or in conjunction with the lubricant 134. The seal assembly 128 may be configured so that the heat that may be created by the high contact-pressure seal 132 may be dissipated into the lubricant 134 and/or housing 112 and/or 104. The low contact-pressure seal 130 may be configured to keep the lubricant in place and create a light seal between the lubricant and the blood. In embodiments, it is expected that some leaking through the low contact-pressure seal 130 between the blood and lubricant 134 may occur. The seal assembly 128 may be configured so that this leakage is minimal and that temperatures around the low contact-pressure seal 130 are maintained low enough so as to not damage the blood.

A controller (not shown) is operably coupled to the motor 102 and is configured to control the motor 102. The controller may be disposed within the motor housing 104 in embodiments, or, in other embodiments, may be disposed outside the housing 104 (e.g., in a catheter handle, independent housing, etc.). In embodiments, the controller may include multiple components, one or more of which may be disposed within the housing 104. According to embodiments, the controller may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like.

The illustrative circulatory support device 100 shown in FIG. 1 is not intended to suggest any limitation as to the scope of use or functionality of embodiments of the present disclosure. The illustrative circulatory support device 100 also should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
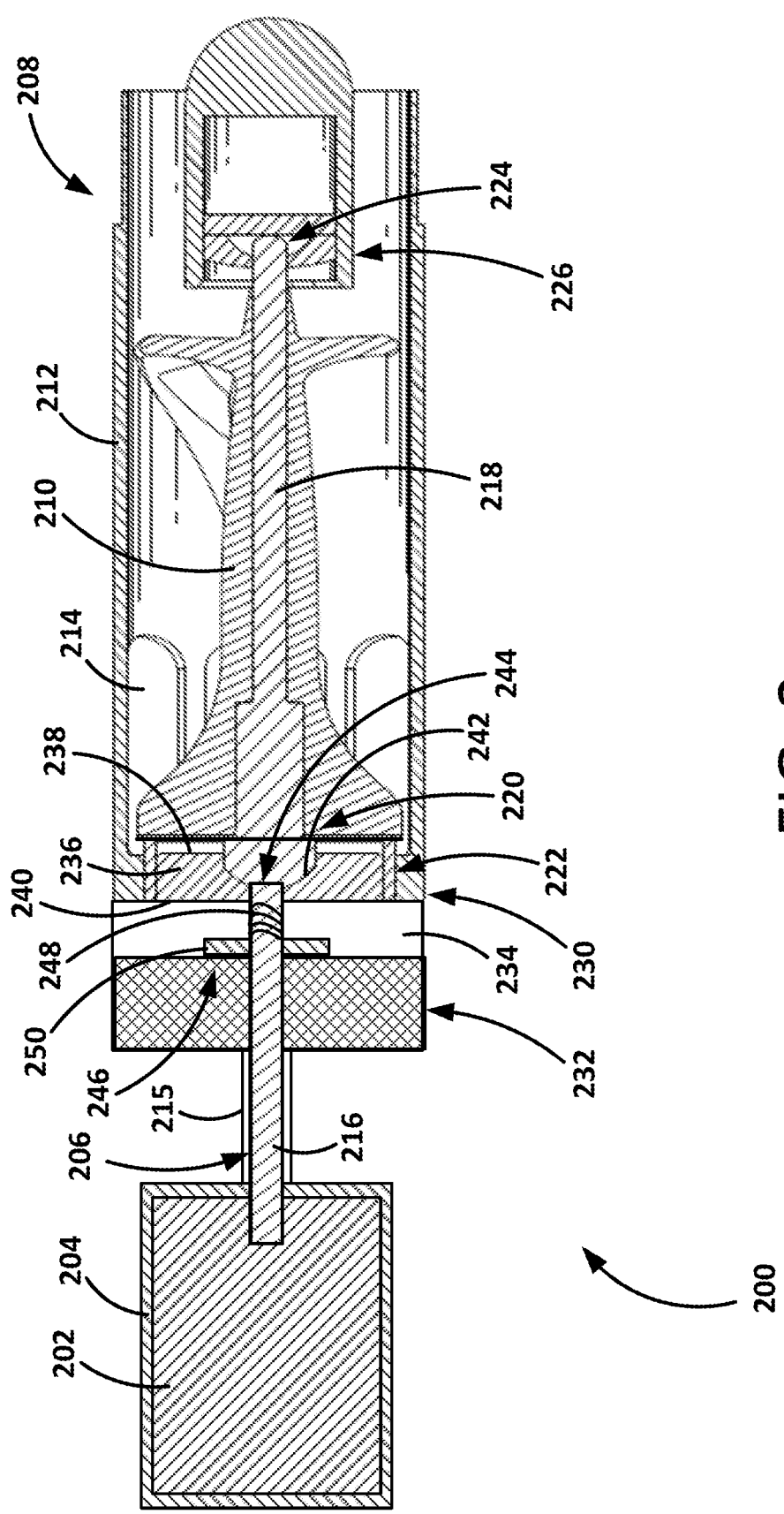
FIG. 2 depicts a cross-sectional side view of a portion of another illustrative mechanical circulatory support device (also referred to herein, interchangeably, as a "blood pump"), in accordance with embodiments of the subject matter disclosed herein.

According to embodiments, the first and second seals may be configured as any number of different types of seals. For example, the seals may be elastomeric rings surrounding the drive shaft, bearings, and/or the like. For example, in embodiments, as shown in FIG. 2, the low contact-pressure seal may be, or include, a cup bearing assembly. FIG. 2 depicts a cross-sectional side view of a portion of an illustrative mechanical circulatory support device 200 (also referred to herein, interchangeably, as a "blood pump"), in accordance with embodiments of the subject matter disclosed herein. According to embodiments, the mechanical circulatory device 200 may be or be similar to the mechanical circulatory device 100 depicted in FIG. 1.

As shown in FIG. 2, the circulatory support device 200 includes a motor 202 disposed within a motor housing 204. The motor 202 is configured to drive, via a drive shaft 206, an impeller assembly 208 to provide a flow of blood through the impeller assembly 208. The impeller assembly 208 includes an impeller 210 disposed within an impeller assembly housing 212, which includes a number of outlet apertures 214 defined therein. The impeller assembly 208 also includes the drive shaft 206 (or at least a portion thereof), where the drive shaft 206 is configured to rotate with the impeller 210. As shown, the drive shaft 206 is at least partially disposed within the impeller 210. In embodiments, the drive shaft 206 may be made of any number of different rigid materials such as, for example, steel, titanium alloys, cobalt chromium alloys, nitinol, high-strength ceramics, and/or the like. In embodiments, the motor 202 may be configured to drive the impeller 210 via a magnetic coupling, rather than via driving the drive shaft 206.

According to embodiments, the motor housing 204 and the impeller assembly housing 212 may be integrated with one another. In other embodiments, the motor housing 204 and the impeller assembly housing 212 may be separate components configured to be coupled together, either removeably or permanently. In still other embodiments, the motor housing 204 may be configured to be separate from the impeller assembly housing 212. For example, in embodiments, the motor housing 204 may be configured to be disposed outside of a subject's body, while the impeller assembly 208 is disposed within the subject's body. In these embodiments, at least a portion of the drive shaft 206 may be configured as a flexible or semi-flexible wire, known as a drive line, which may be disposed within a protective tube 215 that extends from the motor housing 204 to the impeller assembly housing 212. That is, for example, a first portion 216 of the drive shaft 206 may be a wire configured to extend from the motor 202 to the impeller assembly 208, where it is coupled to a second portion 218 of the drive shaft 206, which may, in embodiments, be configured as a solid shaft extending through at least a portion of the impeller 210.

As shown, the impeller 210 is maintained in its orientation by the drive shaft 206 (or, in the case of wire-driven impeller assemblies 208, the second portion 218 of the drive shaft 206), which is retained, at a first end 220, by a first bearing assembly 222 and, at a second end 224, by a second bearing assembly 226. According to embodiments, the first bearing assembly 222 and the second bearing assembly 226 may include different types of bearings. According to embodiments, the first bearing assembly 222 and/or the second bearing assembly 226 may include lubrication, while, in other embodiments, one and/or the other may not include lubrication.

According to embodiments, the device 200 may include a seal assembly 228 having a plurality of seals configured to seal the motor 202, at least a portion of the drive shaft 206, and/or one or more bearings from the blood. According to embodiments, the plurality of seals may include seals of different contact pressures, which may include, for example, high contact-pressure seals and low contact-pressure seals. For example, in embodiments, the impeller assembly 208 may include a first seal 230 and a second seal 232. A volume of lubricant 234 may be disposed between the first seal 230 and the second seal 232. In embodiments, the first seal 230 may be a low contact-pressure seal and the second seal 232 may be a high contact-pressure seal.

As shown, the first seal 230 may be the first bearing assembly 222, and may include a cup bearing 236 and may function as a first (low contact-pressure) seal. As shown in FIG. 2, the cup bearing 236 includes a first side 238, facing toward the impeller assembly 210, and an opposite, second side 240, facing toward the motor 202. A concave depression 242 is defined in the first side 238 of the bearing 236. The concave depression 242 is configured to receive the first end 220 of the drive shaft 206 (or second portion 218 thereof). As shown, the first end 220 of the drive shaft 206 (or second portion thereof 218) may be at least partially rounded and, in embodiments, may include a curvature corresponding to the curvature of the concave depression 242. In this manner, the surface area of contact between the drive shaft 206 (or second portion 218 thereof) and the bearing 236 may be as small as possible, reducing the chance that any blood cells will be able to get between the drive shaft 206 (or second portion 218 thereof) and the bearing 236 at their interface. Additionally, as shown, a shaft aperture 244 may be defined through the bearing 236, extending from the second side 240 to the first side 238, and configured to receive a portion of the drive shaft 206 therein.

According to embodiments, the seal assembly 228 may also include a biasing feature 246 disposed between the second side 240 of the bearing 236 and the motor 202 or the first portion 216 of the drive shaft 206. The biasing feature 246 may have a compliance configured such that the biasing feature 246 biases the bearing 236 in the direction of the impeller 210, while allowing enough flexibility to prevent the bearing 236 from being cracked or otherwise broken by the load. The biasing feature 246 may include, for example, a spring 248 disposed between a spring retainer 250 and the second side 240 of the bearing 236. The spring 248 may be configured to surround a portion of the drive shaft 206. The spring retainer 250 may be integrated into the motor housing 204, the impeller assembly housing 212, coupled to the drive shaft 206, coupled to the second seal 232, and/or the like.

The illustrative circulatory support device 200 shown in FIG. 2 is not intended to suggest any limitation as to the scope of use or functionality of embodiments of the present disclosure. The illustrative circulatory support device 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A seal assembly configured to seal a portion of a blood pump from the blood, the seal assembly comprising:
   a first seal;

a second seal, the second seal comprising a higher contact-pressure seal than the first seal;

wherein the seal assembly is positioned within the blood pump and the blood pump includes at least an impeller;

a drive shaft coupled to the impeller, the drive shaft having a first portion with a first end and a second portion with a second end, and a motor configured to drive the impeller; and wherein the first seal comprises a bearing configured to receive at least one of the first end of the first portion and the second end of the second portion of the drive shaft of the blood pump.

2. The seal assembly of claim 1, further comprising a volume of lubricant disposed between the first seal and the second seal.

3. The seal of assembly of claim 2, wherein the seal assembly is configured so that heat created by the second seal is dissipated into the lubricant and/or a housing of the blood pump.

4. The seal assembly of claim 1, wherein the second end of the second portion of the drive shaft is at least partially rounded, and the bearing comprises a concave depression defined in a first side of the bearing, wherein the depression is configured to receive the second end of the second portion of the drive shaft.

5. The seal assembly of claim 4, the bearing further comprising a shaft aperture defined therein, extending from the second side of the bearing to the first side of the bearing, wherein the shaft aperture is configured to receive at least the first portion or the second portion of the drive shaft.

6. The seal assembly of claim 1, further comprising a biasing feature configured to bias the bearing toward the impeller.

7. The seal assembly of claim 6, the biasing feature comprising a spring disposed between the second side of the bearing and a spring retainer, wherein the spring surrounds a portion of the drive shaft.

8. The seal assembly of claim 1, wherein the seal assembly is disposed in an impeller assembly housing, wherein a drive shaft, having a first portion and a second portion, extends between the impeller assembly housing and a motor housing, wherein the first portion is a drive line disposed within a protective tube, the drive line extending between the motor housing and the impeller assembly housing, wherein the seal assembly is configured to seal the drive line from the blood.

9. A blood pump, comprising:
an impeller assembly having an impeller disposed within an impeller assembly housing;
a drive shaft coupled to the impeller and configured to rotate with the impeller, the drive shaft having a first portion having a first end and a second portion have a second end;
a motor, disposed within a motor housing and configured to drive the impeller;
a seal assembly comprising a plurality of seals, the plurality of seals comprising a first seal and a second seal, the second seal comprising a higher contact-pressure seal than the first seal; and wherein the first seal comprises a bearing configured to receive at least one of the first end of the first portion and the second end of the second portion of the drive shaft.

10. The blood pump of claim 9, further comprising a volume of lubricant disposed between the first seal and the second seal.

11. The blood pump of claim 10, wherein the seal assembly is configured so that heat created by the second seal is dissipated into the lubricant and/or impeller assembly housing.

12. The blood pump of claim 9, wherein the second end of the second portion of the drive shaft is at least partially rounded, and the bearing comprises a concave depression defined in a first side of the bearing, wherein the depression is configured to receive the second end of the second portion drive shaft.

13. The blood pump of claim 12, the bearing further comprising a shaft aperture defined therein, extending from the second side of the bearing to the first side of the bearing, wherein the shaft aperture is configured to receive at least one of the first portion and the second portion of the drive shaft.

14. The blood pump of claim 9, further comprising a biasing feature configured to bias the bearing toward the impeller.

15. The blood pump of claim 14, the biasing feature comprising a spring disposed between the second side of the bearing and a spring retainer, wherein the spring surrounds a portion of the drive shaft.

16. The blood pump of claim 9, wherein the motor housing is coupled to the impeller assembly housing, wherein the seal assembly is configured to seal the motor from the blood.

17. The blood pump of claim 9, wherein the motor housing is separate from the impeller assembly housing, the drive shaft comprising a first portion and a second portion, wherein the first portion is a drive line disposed within a protective tube, the drive line extending between the motor housing and the impeller assembly housing, wherein the seal assembly is configured to seal the drive line from the blood.

18. A blood pump, comprising:
an impeller assembly having an impeller disposed within an impeller assembly housing;
a drive shaft coupled to the impeller and configured to rotate with the impeller, the drive shaft having a first portion including a first end and a second portion including a second end;
a motor, disposed within a motor housing and configured to drive the drive shaft;
a seal assembly disposed within the impeller assembly housing and comprising a plurality of seals, the plurality of seals comprising a first seal and a second seal, the second seal comprising a higher contact-pressure seal than the first seal; and
wherein the first seal comprises a bearing configured to receive at least one of the first end of the first portion and the second end of the second portion of the drive shaft.

* * * * *